United States Patent [19]

Chevion

[11] Patent Number: 5,075,469

[45] Date of Patent: Dec. 24, 1991

[54] PHARMACEUTICAL COMPOSITIONS CONTAINING A ZINC COMPLEX

[75] Inventor: Mordechai Chevion, Jerusalem, Israel

[73] Assignee: Yissum Research Development Company of the Hebrew University of Jerusalem, Jerusalem, Israel

[21] Appl. No.: 550,462

[22] Filed: Jul. 10, 1990

[30] Foreign Application Priority Data

Jul. 19, 1989 [IL] Israel .................................... 91047

[51] Int. Cl.$^5$ .................... C07F 3/00; A61K 9/58; A61K 9/48
[52] U.S. Cl. .................... 556/134; 424/641; 424/642; 424/643; 514/494; 514/332; 562/558
[58] Field of Search .................. 556/134; 562/558; 514/491, 332; 424/643, 641, 642

[56] References Cited

U.S. PATENT DOCUMENTS 2,554,690  5/1951  Wintersteiner .

FOREIGN PATENT DOCUMENTS 0325559  7/1989  European Pat. Off. .
1093445  12/1967  United Kingdom .

OTHER PUBLICATIONS

Alfred Delville and Christian Detellier, "Zn(II)-D-(-)-Penicillamine Complexes in Aqueous Solution, Zn-67 Nuclear Magnetic Resonance Study", Can. J. Chem., vol. 64, pp. 1845-1849, 1986.
Chemical Abstracts, vol. 91, 1979, p. 251, Abstract No. 206347f, Columbus, Ohio, U.S.; L. MacDonald et al.: "Copper and Zinc Complexes of Schiff Base Ligands Containing Penicillamine", Inorg. Chim. ACTA 1979, 33(2), L183.

*Primary Examiner*—Paul J. Killos
*Assistant Examiner*—Nazario-Gonzalez Porfirio
*Attorney, Agent, or Firm*—Fleit, Jacobson, Cohn, Price, Holman & Stern

[57] ABSTRACT

The invention provides a pharmaceutical composition comprising a zinc complex of desferrioxamine or penicillamine as active ingredient therein in combination with a pharmacologically acceptable carrier.

7 Claims, No Drawings

PHARMACEUTICAL COMPOSITIONS CONTAINING A ZINC COMPLEX

The present invention relates to a pharmaceutical composition containing a zinc complex as active ingredient therein. More particularly the present invention relates to pharmaceutical preparations which are effective against iron-mediated damage, said preparations being based on zinc complexes with desferrioxamine B or with penicillamine.

Redox-active iron and copper have been demonstrated to be responsible for tissue damage in ischemia and reperfusion injury, thallesemia, hemochromatosis and Wilson disease. Furthermore, in a wide variety of pathologic states the causative role of free radicals has been proposed. These metals can readily serve as effective mediators enhancing free radical induced damage, and thus, have been incriminated as a major responsible species for tissue injury. (M. Chevion: A site specific mechanism for free radical induced biological damage: The essential role of redox active transition metals. Free Radical for Biology and Medicine, 5(1), 27–37, 1988).

The present inventors have shown that the use of desferrioxamine and better still, the combination of desferrioxamine and nitrilotriacetate (NTA) resulted in a dramatic increase in the rate of survivors in paraquat toxicity. While in control group there were no survivors, following treatment with either chelators, 25-30% survivors were monitored. The administration of a combination of these specific chelators led to 60-90% survivors (average 70%). (R. Kohen and M. Chevion. Paraquat toxicity is enhanced by iron and inhibited by desferrioxamine in laboratory mice. Biochemistry Pharmacology 34, 1841–1843, 1985).

Similarly, the present inventors have shown that neocuproine, a chelator that effectively binds iron and copper and easily penetrates into cells, provides marked protection against ischemic-induced arrhythmias in the isolated rat heart using the Langendoff configuration. (Y. J. Appelbaum, G. Uretsky and M. Chevion: The protective effect of neocuproine on cardiac injury induced by oxygen active species in the presence of copper sulphate. Journal of Molecular and Cellular Cardiology 19 (Supp. III) Abstract #8, 1987; J. Kuvin, Y. J. Appelbaum. M. Chevion, J. B. Borman and G. Uretzky: Role of oxygen free radicals in reperfusion induced arrhythmias: protection by neocuproine. Journal of Molecular and Cellular Cardiology, 19 (Supp. III). Abstract #150, 1987, Y. J. Appelbaum, J. Kuvin, J. B. Borman, G. Uretzky and M. Chevion: Role of oxygen free radicals in reperfusion-induced arrhythmias: protection by neocuproine. Free Radicals in Biology and Medicine, 8, 133–143, 1990).

According to the present invention it has now been found that the complex Zn-desferrioxamine possesses characteristics which markedly improve the pharmaceutical efficacy of Desferal. This is achieved by markedly enhancing its permeability into cells, and by the consequent significant increase of its capacity to bind intracellular iron and copper. In these chelates the transition metals are not redox-active and cannot mediate free radical production. Concomitantly with the binding of copper and iron, "free" zinc is released from its complex with Desferal or penicillamine, in a controlled mode that is fully dependent on the level of cell saturation with "free" iron and copper. As zinc is a relatively abundant trace element, and is also approved as an oral nutritional supplement, and as desferrioxamine is an approved drug (patent protection expired). the approval of this combination for clinical trials for treatment of ischemic injury, thallesemics, in cases of paraquat intoxication, and in other instances where free radicals are implicated should smoothly be carried through. Additionally, the Zn-desferrioxamine complex is highly permeable, and thus, can be administered orally, providing a prominent advantage over the current procedures for administering Desferal. This is also true for the complex with penicillamine, which is usually given per os.

Thus, the present invention provides a pharmaceutical composition comprising a zinc complex of desferrioxamine or penicillamine as active ingredient therein in combination with a pharmacologically acceptable carrier.

As reported by H. Keberle: Biochemistry of desferrioxamine and its relation to iron metabolism. Annals of the New York Academy of Sciences, 119, 758–762, 1964. the desferrioxamine molecule is made up from six basic units. In this form, when it is not bound to metals, it is a linear molecule, that cannot easily penetrate into most cells. (R. Laub, Y. J. Schneider, J. N. Octave, A. Trouet and R. R. Crichton: Cellular pharmacology of desferrioxamine B and derivatives in cultured rat hepatocytes in relation to iron mobilization. Biochemistry Pharmacology 34, 1175–1183, 1985).

In contrast, upon metal bindings (such as in ferrioxamine) it forms a globular complex. In addition to iron, desferrioxamine forms tight complexes with copper and zinc. Based on the similarity of the ligand chemistry between iron or copper, on one hand, and zinc on the other, it is reasonable to assume that the structure of zinc-desferrioxamine is also spherical (rather than linear). In addition, metal binding to the negatively charged desferrioxamine renders the molecule less polar. These considerations might explain why the complexes more easily penetrate through cellular membranes and biological barriers, and more effectively bind intracellular metals that are redox active and mediate tissue damage. In this process two steps provide antioxidant protection: a) the removal of redox-active iron and copper by their chelation, and b) the controlled release of "free" zinc, that in itself possesses anti-oxidant activity.

The relative stability constants for the complexes of desferrioxamine with Fe(III), Cu(II) and Zn(II) are $10^{31}$, $10^{14}$ and $10^{11}$ respectively. Thus, based on these thermodynamic considerations, upon penetration into cells, with high abundance of low molecular weight and redox-active complexes of iron or copper, the Zn-desferrioxamine complex exchanges the Zn with iron or copper. In addition to the exchange of zinc for iron or copper, the newly released zinc could have an additional beneficial anti-oxidant effect, as has already been shown in a few systems such as described, e.g., by D. E. Copper, D. E. Richardson and R. J. Cousins: Zinc suppression of free radicals induced in cultures of rat hepatocytes by iron, t-butyl hydroperoxide and 3-methylindole, Proceedings of the Society for Experimental Biology and Medicine 189, 100–109, 1988.

The present preparations should contain the following components:

A. For treatment by injection:
 1. $ZnCl_2$/Desferal ® (molar ratios Zn/Desferal ® between 0.1/1.0 and 1.25/1.0) in isotonic solution.

B. For oral use: capsules, tablets, or drinkable preparation should contain:
1. Zn/Desferal ® (molar ratios between 0.60/1.0 and 1.25/1.0)
2. $ZnCl_2$/penicillamine (molar ratios Zn/penicillamine 0.1/1.0 and 1.25/1.0).

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

Example 1: Zn/Desferal complex (MJC-1)

10 mM solution of Desferal (Ciba Geigy, Basle) is mixed with an equal volume of 6 mM of $ZnCL_2$ (A. R. Aldrich Chemical Co., Inc.) solution, titrated to pH 7.4. The mixture is heated for 30 min. to 45° C., and cooled and the complex Zn/Desferrioxamine B is formed. The ratio Zn:Desferal is 0.6:1.0.

Example 2: Zn Desferal complex (MCJ-2)

10 mM solution of Desferal (Ciba-Geigy, Basle) is mixed with an equal volume of 10 mM solution of $ZnCl_2$ (A. R. Aldrich Chemical Co., Inc.) solution, titrated to pH 7.4. The mixture is heated for 30 min. to 45° C., and cooled and the complex Zn/Desferrioxamine B is formed. The ratio Zn:Desferal is 1.0:1.0.

Example 3: Zn/Desferal complex (MCJ-3)

10 mM solution of Desferal (Ciba-Geigy, Basle) is mixed with an equal volume of 12.5 mM of $ZnCl_2$ (A. R. Aldrich Chemical Co., Inc.) solution, with 10 ml of 5.5 mM Histidine, titrated to pH 7.4. The mixture is heated for 30 min. to 45° C., and cooled and the complex Zn/Desferrioxamine B is formed, the ratio Zn:Desferal is 1.25:1.0

Example 4: Zn/Desferal complex IV 50 mM solution of Desferal (Desferrioxamine B) is mixed with 1/5 the volume of 50 mM solution of $ZnSO_4$ (zinc sulfate heptahydrate, Aldrich Chemical Co., Inc.). The mixture is heated to for 45 min. to 40° C. and cooled to form the resultant Zn/Desferrioxamine (5 nM) complex. The ratio Zn/Desferal is 0.2:1.0

Example 5: Zn/Desferal complex

To the dry contents of 1 vial (500 mg, 0.76 mmole) of Desferrioxamine B, 168 mg of dry zinc acetate dihydrate (0.76 mmole) are added. Doubly distilled water is added until the contents fully dissolve (~10 ml). Warm to 40° C. for 45 minutes, cool down and the complex Zn/Desferal (1.0:1.0) is ready to be used.

Example 6: Zn/Penicillamine complex

D-penicillamine (Aldrich Chemical Co., Inc.) 30 mM in doubly distilled water is mixed with equal volume of 30 mM $ZnCl_2$ (Aldrich Chemical Co., Inc.). The mixture is heated to 45° C. for 30 minutes, cooled and the complex Zn/penicillamine (1.0:1.0)is formed.

Example 7: Zn/Penicillamine complex 149.2 mg of solid D-penicillamine (Aldrich Chemical Co., Inc.) and 219.5 mg of zinc acetate dihydrate (Aldrich Chemical Co., Inc.) are dissolved in a minimum volume of doubly distilled water (~12 ml), heated to 40° C. for 45 minutes, and cooled to room temperature to form the complex Zn/penicillamine.

Example 8: Zn/Penicillamine complex

To 50 mM solution of D-penicillamine in doubly distilled water, are added 1/5 of the volume of 500 mM zinc sulfate heptahydrate (Aldrich Chemical Co., Inc.). The pH is adjusted to 5.5, the mixture is heated to 45° C. for 30 minutes and then cooled. A 42 mM solution of Zn/penicillamine is then used.

Example 9: Pharmaceutical preparation of Zn/Desferal complex for i.v. injection A zinc chloride solution (7.6 mM) in sterile saline is prepared by dissolving 1.043 gm of high purity zinc chloride (Aldrich Chemical Co., Inc.) in one liter of saline, autoclaving and cooling to room temperature. 10 ml of the zinc chloride sterile solution is added to a vial of 500 mg of Desferal, the mixture is shaken until the contents are completely dissolved and used for either a bolus or continuous injection.

Example 10: Pharmaceutical preparation of Zn/Desferal complex for oral administration 10 ml of sterile solution containing 500 mg Desferal, 10.4 mg zinc chloride and 1 gr of glucose is prepared by dissolving the contents of one vial of Desferal in $ZnCl_2$/glucose sterile solution.

Example 11: Pharmaceutical preparation of Zn/pencillamine complex oral administration 250 mg of D-penicillamine is dissolved in doubly distilled water, 228.3 mg zinc chloride are added, and the solution is heated to 40° C. for 45 minutes, cooled to room temperature and then lyophilize-dried. The solid is finely pulverized and inserted into a commercial gelatin capsule.

Example 12: Pharmaceutical preparation of Zn/Pencillamine complex for oral administration 250 mg of D-penicillamine and 228.3 mg zinc chloride are dissolved in doubly distilled water, heated to 45° C. for 30 minutes, cooled to room temperature and lyophilize-dried. The solid is collected, finely pulverized, and compressed into a tablet using commercial binders and disintegrators.

Example 13: MCJ-3 protects against cardiac damage to the isolated rat heart in the Langendorff configuration The experiments and analysis were conducted in an analogous mode as described in S. Powell, P. Saltman, G. Uretzky and M. Chevion: The effect of zinc on reperfusion arrhythmias in the isolated perfused rat heart. Free Radical Biology & Medicine 8, 33–46, 1990. Following 10 min. of steady state (stabilization) the LAD is occluded for 10 min. and then reopened. The protection observed, in the reperfusion phase, with 15 μM (micromolar) MCJ-3 is 40%, 58% and 47% for P (peak left ventricular pressure), +dP/dt and −dP/dt, respectively. Additionally, 15μM MCJ-3 provided complete (100%) protection against reperfusion-induced arrhythmias.

Example 14: MCJ-2 protects bacterial cells against copper-mediated paraquat-induced killing 1–10 μM (micromolar) of MCF-2 provides protection against the toxicity of paraquat to E. coli cells at the range of 39–73% as indicated by reduced killing. The experiments and analysis were conducted in an analogous mode to that described in P. Korbashi, J. Katzhendler, P. Saltman and M. Chevion: Zinc protects *E. coli* against copper-mediated paraquat-induced damage. Journal of Biological Chemistry, 264, 8479–8482, 1989.

Example 15: MCJ-2 protects against paraquat toxicity in Balb C male mice

Groups of 10 animals were injected with 35 mg/kg paraquat which lead to death in all animals within 4–5 days. A course of treatment of the mice with MCJ-2 lead to 20–30% survivors. The course of treatment included injection of the drug i.p. at 1 hour following intoxication with paraquat (25 mg/kg), followed by 3 injections of 50 mg/kg every 8 hours. The experiments and analysis were conducted in an analogous mode to that described in R. Kohen and M. Chevion: Paraquat toxicity is enhanced by iron and inhibited by desferrioxamine in laboratory mice. Biochemical Pharmacology 34, 1841–1843, 1985.

Example 16: Displacement of zinc within Zn/desferrioxamine complex by iron taken Zn/desferrioxamine complex (0.2 mM) was prepared and its spectrum taken. Small volume aliquots of ferric chloride ($FeCl_3$, 100 mM) were added to reach a final concentration of Fe(III)0.05–0.20 mM. Spectrophotometric examination shows the immediate formation of a stoichiometric complex of ferric-desferrioxamine which has a characteristic absorbance of 425 nm.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A pharmaceutical composition, comprising, in a pharmaceutically acceptable carrier, a zinc complex of desferrioxamine.

2. A pharmaceutical composition for the treatment of free radical induced pathological conditions, comprising, in a pharmaceutically acceptable carrier, a zinc complex of desferrioxamine.

3. A pharmaceutical composition for the treatment of injury resulting from ischemic insult to the heart, brain or kidney, comprising, in a pharmaceutically acceptable carrier, a zinc complex of desferrioxamine.

4. A pharmaceutical composition for the treatment of paraquat toxicity, comprising, in a pharmaceutically acceptable carrier, a zinc complex of desferrioxamine.

5. A pharmaceutical composition for exchanging zinc for iron, comprising, in a pharmaceutically acceptable carrier, a zinc complex of desferrioxamine.

6. A pharmaceutical composition according to claim 1 suitable for injection and comprising a complex of $ZnCl_2$ and desferrioxamine in a molar ratio of about between 0.1:1.0 and 1.0:1.0 in isotonic solution.

7. A zinc desferrioxamine complex.

* * * * *